(12) United States Patent
Ma

(10) Patent No.: US 10,568,468 B2
(45) Date of Patent: Feb. 25, 2020

(54) FLUID PUMP STERILIZATION APPARATUS AND METHOD

(71) Applicant: Richard Ma, Carlisle, MA (US)

(72) Inventor: Richard Ma, Carlisle, MA (US)

( * ) Notice: Subject to any disclaimer, the term of this patent is extended or adjusted under 35 U.S.C. 154(b) by 0 days.

(21) Appl. No.: 16/249,778

(22) Filed: Jan. 16, 2019

(65) Prior Publication Data
US 2019/0142227 A1 May 16, 2019

Related U.S. Application Data

(63) Continuation of application No. 15/370,612, filed on Dec. 6, 2016, now Pat. No. 10,231,579, which is a continuation of application No. PCT/US2016/033727, filed on May 23, 2016.

(60) Provisional application No. 62/165,076, filed on May 21, 2015.

(51) Int. Cl.
| | | |
|---|---|---|
| *B05B 11/00* | (2006.01) | |
| *A47K 5/12* | (2006.01) | |
| *B05B 1/14* | (2006.01) | |
| *A61L 2/00* | (2006.01) | |
| *A61L 2/18* | (2006.01) | |

(52) U.S. Cl.
CPC .......... *A47K 5/1205* (2013.01); *A61L 2/0088* (2013.01); *A61L 2/18* (2013.01); *B05B 1/14* (2013.01); *B05B 11/0044* (2018.08); *B05B 11/3001* (2013.01); *B05B 11/306* (2013.01); *B05B 11/3084* (2013.01); *A61L 2202/15* (2013.01); *A61L 2202/17* (2013.01); *A61L 2202/24* (2013.01)

(58) Field of Classification Search
CPC . A61L 2202/24; A61L 2202/17; A61C 5/064; B05C 17/01; B05C 17/002; B05C 1/14; B05C 11/3001; B05C 11/306; B65D 81/325
USPC ............................ 222/381.1, 137; 401/188 R
See application file for complete search history.

(56) References Cited

U.S. PATENT DOCUMENTS

| | | | | |
|---|---|---|---|---|
| 6,968,982 B1 * | 11/2005 | Burns | ................... | B65D 83/26 222/135 |
| 8,690,020 B1 * | 4/2014 | Murray | ................... | F41H 9/10 222/113 |
| 2007/0295754 A1 * | 12/2007 | Tourigny | ........... | B05B 11/3052 222/205 |

* cited by examiner

*Primary Examiner* — Paul R Durand
*Assistant Examiner* — Robert K Nichols, II
(74) *Attorney, Agent, or Firm* — Polsinelli PC

(57) ABSTRACT

An apparatus (10) for pumping first and second selected sterilizing or cleaning fluids (F1, F) by a user comprising: a first fluid container (12), a second fluid container (12k), a first pump assembly (18), a second pump assembly (18k),
the first and second pump assemblies (18, 18k) being interconnected in an arrangement adapted to simultaneously pump the first fluid (F1) through upstream end fluid delivery apertures (22a) and the second fluid (F) through a laterally extending spout (24k) on manual driving of the external device in the downstream direction (D), the first fluid (F1) being delivered to the complementary surface (17s) of an external device (15) separately from the second fluid (F).

8 Claims, 9 Drawing Sheets

FLUID PUMP STERILIZATION APPARATUS AND METHOD

RELATED APPLICATIONS

This application is a continuation of and claims the benefit of priority to U.S. application Ser. No. 15/370,612 filed Dec. 6, 2016 which claims the benefit of priority of U.S. Provisional application Ser. No. 62/165,076 filed May 21, 2015, the disclosures of both which are incorporated by reference as if fully set forth herein.

BACKGROUND

Medical devices, instruments, implements and the like are commonly used by doctors, nurses and health care providers generally on multiple patients. Devices such as stethoscopes, blood pressure measurement devices, electrodes and the like are used to make contact with some portion of the surface of multiple patients one after the other without thought for sterilization in advance of use or, if sterilization is immediately available for use, is ignored by the health care provider due to the seemingly low risk of contamination of the device being used.

SUMMARY OF INVENTION

Health care providers and physicians often see how hospitalization can be harmful to a subject's health. The number of hospital acquired infections are quite alarming. Health care providers are typically very careful to hand wash their hands between attending to successive patients. Health care providers often isolate patients with very resistant infections and sanitize the room when the infected patient is discharged. Notwithstanding such precautions, a major culprit in spreading infection between successive patients is the stethoscope. Health care providers put it around their necks in close proximity to their own exhaled breath.

Stethoscopes physically touch every patient that a health care provider normally sees and rarely is a stethoscope cleaned with alcohol. In a typical day in a hospital every patient is seen by at least 3-4 nurses (due to shift changes), 1-3 physicians (depending on whether a specialist are involved or not), 2-3 nurse's aids (taking vital signs), and possibly a few respiratory therapists. This number is much higher in teaching hospitals because of exposure to medical students and student nurses. The stethoscope touches one patient up to 10 times a day. This means just by random chance a single patient can actually have contact with a total stranger in another floor of the hospital more than once without ever knowing it. Covers for stethoscopes have been devised but have not been practicable in the mechanisms, if any, for accessibility or ease of use.

Although bags or covers have been used for covering stethoscopes such as disclosed in U.S. patent publication no. 20120010517, such bags or devices cannot proactively sterilize a surface of the stethoscope or other medical device prior to its use.

In accordance with the invention there is provided an apparatus 10 for pumping a selected sterilizing fluid F by a user comprising:

a fluid container 12 having an enclosed interior chamber 13 that receives the selected sterilizer fluid,
a pump assembly 18 comprising a base 18b, a fluid delivery tube 20 having an axis A and a central fluid flow channel 20FC, the fluid delivery tube 20 being slidably mounted in the base 18b for reciprocal upstream U, downstream D movement through the base, the fluid delivery tube 20 having an upstream end 22 and being spring load biased S in an upstream direction U such that the upstream end 22 of the fluid delivery tube is urged upstream U to a stationary start position disposed outside the enclosed interior chamber 13,
the fluid delivery tube 20 being manually drivable by the user in a downstream direction D starting from the stationary start position and adapted to pump fluid upstream F1u through the fluid flow channel 20FC on downstream driven movement D of the fluid delivery tube 20,
the upstream end 22 of the fluid delivery tube 20 comprising an enlarged head 22 having an upstream facing surface 22s having one or more apertures 22a disposed in and through the upstream facing surface 22s, the one or more apertures 22a communicating 20c with the fluid flow channel 20FC of the fluid delivery tube 20 such that fluid F1 that resides within the fluid flow channel 20FC is pumped through the one or more apertures 22a on driven movement of the fluid delivery tube in the downstream direction D,
the upstream facing surface 22s of the head being configured to receive and engage a complementary surface 17s of an external device 15 having a predetermined surface contour,
the fluid delivery tube 20 being drivable downstream from the start position by manually engaging the complementary surface 17s of the external device 15 against the upstream facing surface 22s of the enlarged head 22 and manually driving the external device in the downstream direction D.

The upstream end 22 of the fluid delivery tube 20 can include a spout 24 extending in a generally radial direction R from the axis A of the fluid delivery tube 20, the spout 24 having a radial flow channel 24c that terminates at an upstream end in an open fluid delivery aperture 24a and communicates at a downstream end 24b with the fluid flow channel 20FC of the fluid delivery tube 20 such that fluid F1 that resides within the fluid flow channel is pumped through the radial channel 24c on downstream movement D of the fluid delivery tube 20.

The fluid delivery tube 20 is typically adapted to draw fluid F1 that resides in the enclosed container 13 upstream into the fluid flow channel 20FC or into fluid communication with 18cc, 20da the fluid flow channel 20FC on upstream movement U of the fluid delivery tube 20 under force of the spring load bias S exerted on the fluid delivery tube 20.

The fluid flow channel preferably branches 20b at a distribution position into a first branch 20c and a second branch 24c that simultaneously and respectively communicate fluid F to the one or more apertures 22a in the head 22 and to the radial flow channel 24c of the spout 24.

The pump assembly 18 can include a cylinder 18c having an inner wall surface, the fluid delivery tube comprising an elongated tube portion 20et having a piston head 20p formed on a downstream end of the elongated tube 20et, the piston head 20p having an outer circumferential surface 20ps that sealably and slidably mates with the inner wall surface 18ccs of the cylinder 18c to form a downstream fluid receiving chamber 18cc within the cylinder 18c that receives fluid F1u that is resident in the enclosed interior chamber 13 of the container 12 through a downstream valve 60v that is mounted to the cylinder on upstream movement of the fluid delivery tube 20, the fluid received F1 within the fluid receiving chamber 18cc of the cylinder 18c being forced upstream through an aperture 20da that is disposed in the piston head 20p that is in communication with the fluid flow channel 20FC.

In another aspect of the invention there is provided a method of performing a sterilization process comprising a user's manually engaging the upstream facing surface of the head of the apparatus described above with the complementary surface of the selected device and manually driving the fluid delivery tube in the downstream direction by manually driving the selected device in the downstream direction while the complementary surface is engaged with the upstream facing surface of the head.

In another aspect of the invention there is provided an apparatus for pumping a selected sterilizing fluid by a user comprising:

a fluid container having an enclosed interior chamber that receives the selected sterilizer fluid, a pump assembly comprising a base, a fluid delivery tube having an axis and a central fluid flow channel, the fluid delivery tube being slidably mounted in the base for reciprocal upstream, downstream movement through the base, the fluid delivery tube having an upstream end and being spring load biased in an upstream direction such that the upstream end of the fluid delivery tube is urged upstream to a stationary start position disposed outside the enclosed interior chamber, the fluid delivery tube being manually drivable by the user in a downstream direction starting from the stationary start position and adapted to pump fluid upstream through the fluid flow channel on downstream driven movement of the fluid delivery tube, the upstream end of the fluid delivery tube comprising an enlarged head having an upstream facing surface having one or more apertures disposed in and through the upstream facing surface, the one or more apertures communicating with the fluid flow channel of the fluid delivery tube such that fluid that resides within the fluid flow channel is pumped through the one or more apertures on driven movement of the fluid delivery tube in the downstream direction, the upstream facing surface of the head being configured to receive and engage a complementary surface of an external device having a predetermined outer surface contour, wherein the upstream end of the fluid delivery tube includes a spout extending in a generally radial direction from the upstream end of the fluid delivery tube, the spout having a radial flow channel that terminates at an upstream end in an open fluid delivery aperture and communicates at a downstream end with the fluid flow channel of the fluid delivery tube such that fluid that resides within the fluid flow channel is pumped through the radial channel on downstream movement of the fluid delivery tube.

In such an apparatus, the fluid delivery tube is preferably adapted to draw fluid that resides in the enclosed container upstream into the fluid flow channel or into fluid communication with the fluid flow channel on upstream movement of the fluid delivery tube under force of the spring load bias exerted on the fluid delivery tube.

The fluid flow channel typically branches at a distribution position into a first branch and a second branch that simultaneously and respectively communicate fluid to the one or more apertures in the head and to the radial flow channel of the spout.

The pump assembly can include a cylinder having an inner wall surface, the fluid delivery tube comprising an elongated tube having a piston head formed on a downstream end of the elongated tube, the piston head having an outer circumferential surface that sealably and slidably mates with the inner wall surface of the cylinder to form a downstream fluid receiving chamber within the cylinder that receives fluid that is resident in the enclosed interior chamber of the container through a downstream valve that is mounted to the cylinder on upstream movement of the fluid delivery tube, the fluid received within the fluid receiving chamber of the cylinder being forced upstream through an aperture that is disposed in the piston head that is in communication with the fluid flow channel.

In another aspect of the invention there is provided a method of performing a sterilization process comprising a user's manually engaging the upstream facing surface of the head of the apparatus described immediately above with the complementary surface of the selected device and manually driving the fluid delivery tube in the downstream direction by manually driving the selected device in the downstream direction while the complementary surface is engaged with the upstream facing surface of the head.

In another aspect of the invention there is provided an apparatus (10) for pumping first and second selected sterilizing or cleaning fluids (F, F1) by a user comprising:

a first fluid container (12) having an enclosed interior chamber (10c) that receives and contains the first selected sterilizer fluid (F), a second fluid container (12k) having an enclosed interior chamber (10kc) that receives and contains the second selected sterilizer fluid (F1), a first pump assembly (18) comprising a base (18b) mounted to the first fluid container (12), a fluid delivery tube (20) communicating with the fluid contained in the first fluid container (12), the fluid delivery tube (20) having an axis (A) and a central fluid flow channel (20FC), the fluid delivery tube (20) being slidably mounted in the base (18b) for reciprocal upstream (U), downstream (D) movement through the base, the fluid delivery tube (20) having an upstream end (22) and being spring load biased (S) in an upstream direction (U) such that the upstream end (22) of the fluid delivery tube is urged upstream (U) to a stationary start position disposed outside the enclosed interior chamber (13), the fluid delivery tube (20) being manually drivable by the user in a downstream direction (D) starting from the stationary start position and adapted to pump fluid upstream (F1u) through the fluid flow channel (20FC) on downstream driven movement (D) of the fluid delivery tube (20), the upstream end (22) of the fluid delivery tube (20) comprising an enlarged head (22) having an upstream facing surface (22s) having one or more apertures (22a) disposed in and through the upstream facing surface (22s), the one or more apertures (22a) communicating (20c) with the fluid flow channel (20FC) of the fluid delivery tube (20) such that fluid (F1) that resides within the fluid flow channel (20FC) is pumped through the one or more apertures (22a) on driven movement of the fluid delivery tube in the downstream direction (D), the upstream facing surface (22s) of the head being configured to receive and engage a complementary surface (17s) of an external device (15) having a predetermined surface contour, the fluid delivery tube (20) being drivable downstream from the start position by manually engaging the complementary surface (17s) of the external device 15 against the upstream facing surface (22s) of the enlarged head (22) and manually driving the external device in the downstream direction (D).

In such an apparatus the first fluid container (12) and the second fluid container (12k) are preferably adapted such that an undersurface (24u) of a laterally extending spout (24) of the first fluid container (12) engages a top surface (22k) of a laterally extending spout (24k) of the second fluid container (12k) that is interconnected to a second fluid delivery tube (20k) that is interconnected to a second pump assembly (18k) wherein both the first and second fluid delivery tubes (20, 20k) are simultaneously manually drivable by the user in a downstream direction (D) starting from the stationary start position and adapted to pump both fluids (F, F1) upstream (F1u) respectively through respective fluid delivery apertures 22a, 24a on downstream driven movement (D) of the fluid delivery tubes (20, 20k).

In another aspect of the invention there is provided a method of performing a sterilization or cleaning process comprising a user's manually engaging the upstream facing surface (22s) of the head (22) of the pump assembly (18) of the apparatus as described immediately above with the complementary surface (17s) of the selected device (15) and manually driving the first fluid delivery tube (20) in the downstream direction by manually driving the selected device (15) in the downstream direction while the complementary surface is engaged with the upstream facing surface of the head.

In another aspect of the invention there is provided an apparatus (10) for pumping first and second selected sterilizing or cleaning fluids (F, F1) by a user comprising:
a fluid container (500) having a first enclosed interior chamber (10c) that receives and contains a first selected sterilizer or cleaning fluid (F) and a second enclosed interior chamber (10kc) that receives and contains a second selected sterilizer or cleaning fluid (F1),
a first pump assembly (18) comprising a base (18b) mounted to the first fluid container (500), a fluid delivery tube (20) communicating with the fluid (F) contained in the first enclosed interior chamber (10c), the fluid delivery tube (20) having an axis (A) and a central fluid flow channel (20FC), the fluid delivery tube (20) being slidably mounted in the base (18b) for reciprocal upstream (U), downstream (D) movement through the base, the fluid delivery tube (20) having an upstream end (22) and being spring load biased (S) in an upstream direction (U) such that the upstream end (22) of the fluid delivery tube is urged upstream (U) to a stationary start position disposed outside the enclosed interior chamber (13),
the fluid delivery tube (20) being manually drivable by the user in a downstream direction (D) starting from the stationary start position and adapted to pump fluid upstream (F1u) through the fluid flow channel (20FC) on downstream driven movement (D) of the fluid delivery tube (20),
the upstream end (22) of the fluid delivery tube (20) comprising an enlarged head (22) having an upstream facing surface (22s) having one or more apertures (22a) disposed in and through the upstream facing surface (22s), the one or more apertures (22a) communicating (20c) with the fluid flow channel (20FC) of the fluid delivery tube (20) such that fluid (F1) that resides within the fluid flow channel (20FC) is pumped through the one or more apertures (22a) on driven movement of the fluid delivery tube in the downstream direction (D),
the upstream facing surface (22s) of the head being configured to receive and engage a complementary surface (17s) of an external device (15) having a predetermined surface contour,
the fluid delivery tube (20) being drivable downstream from the start position by manually engaging the complementary surface (17s) of the external device 15 against the upstream facing surface (22s) of the enlarged head (22) and manually driving the external device in the downstream direction (D),
the second selected fluid (F1) being simultaneously pumped through an exit aperture 24a disposed at the end of a spout (24k) communicating with the second interior chamber 10kc on downstream driven movement of the fluid delivery tube (20).

Such an apparatus of preferably further comprises a second fluid delivery tube (20k) communicating with the spout (24k) and being interconnected to a second pump assembly (18k) wherein both the first and second fluid delivery tubes (20, 20k) are simultaneously manually drivable by the user in a downstream direction (D) starting from the stationary start position and adapted to pump both fluids (F, F1) upstream (F1u) respectively through respective fluid delivery apertures 22a, 24a on downstream driven movement (D) of the fluid delivery tubes (20, 20k).

In another aspect of the invention there is provided a method of performing a sterilization or cleaning process comprising a user's manually engaging the upstream facing surface (22s) of the head (22) of the pump assembly (18) of the apparatus described immediately above with the complementary surface (17s) of the selected device (15) and manually driving the first fluid delivery tube (20) in the downstream direction by manually driving the selected device (15) in the downstream direction while the complementary surface is engaged with the upstream facing surface of the head.

DETAILED DESCRIPTION OF INVENTION

Figure 1:
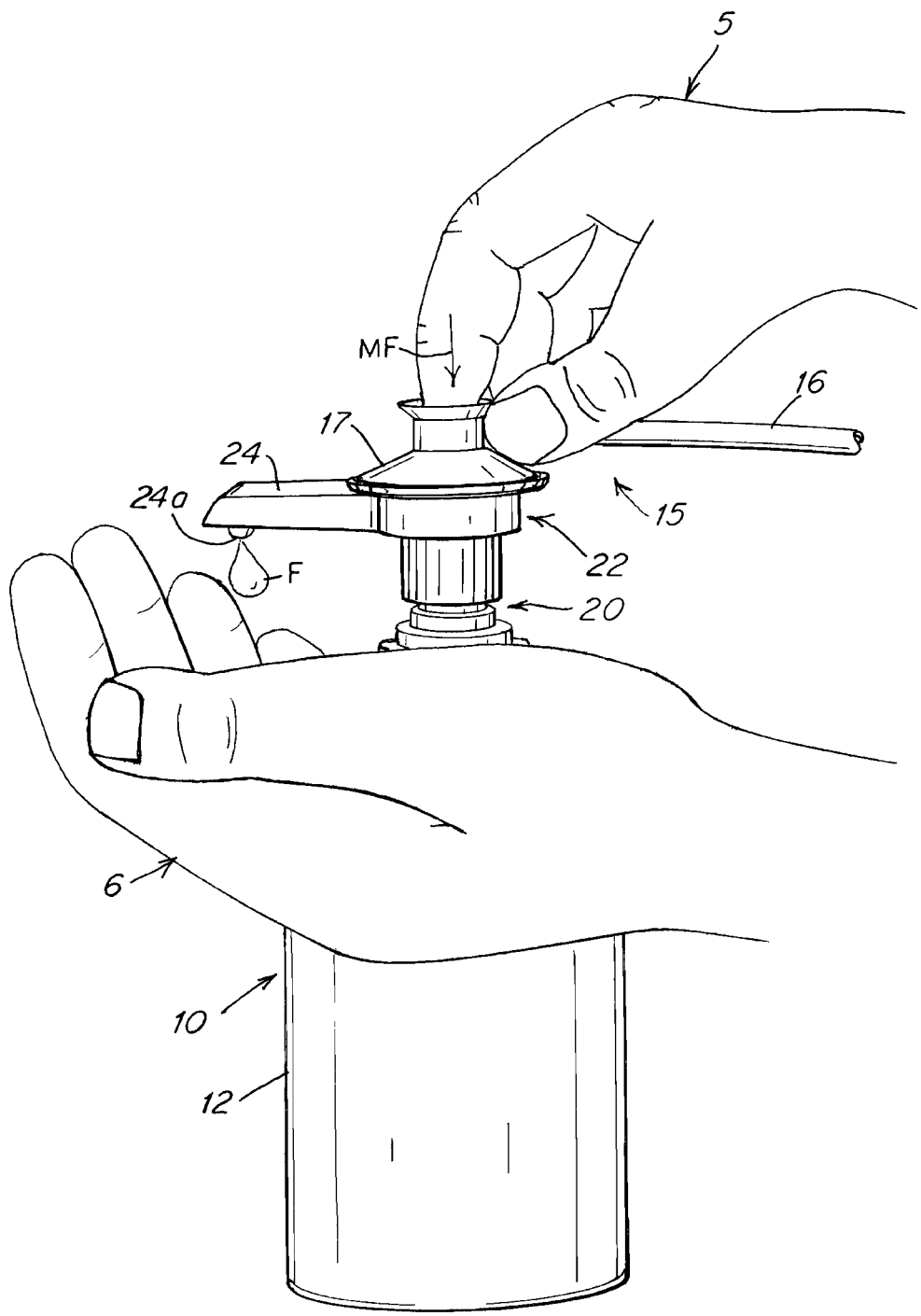
FIG. 1 is a side perspective view of an apparatus according to the invention showing a user exerting a downstream force on a medical device that is engaged with the upstream downstream drivable fluid delivery tube component of the pump assembly of the apparatus.
Figure 2:
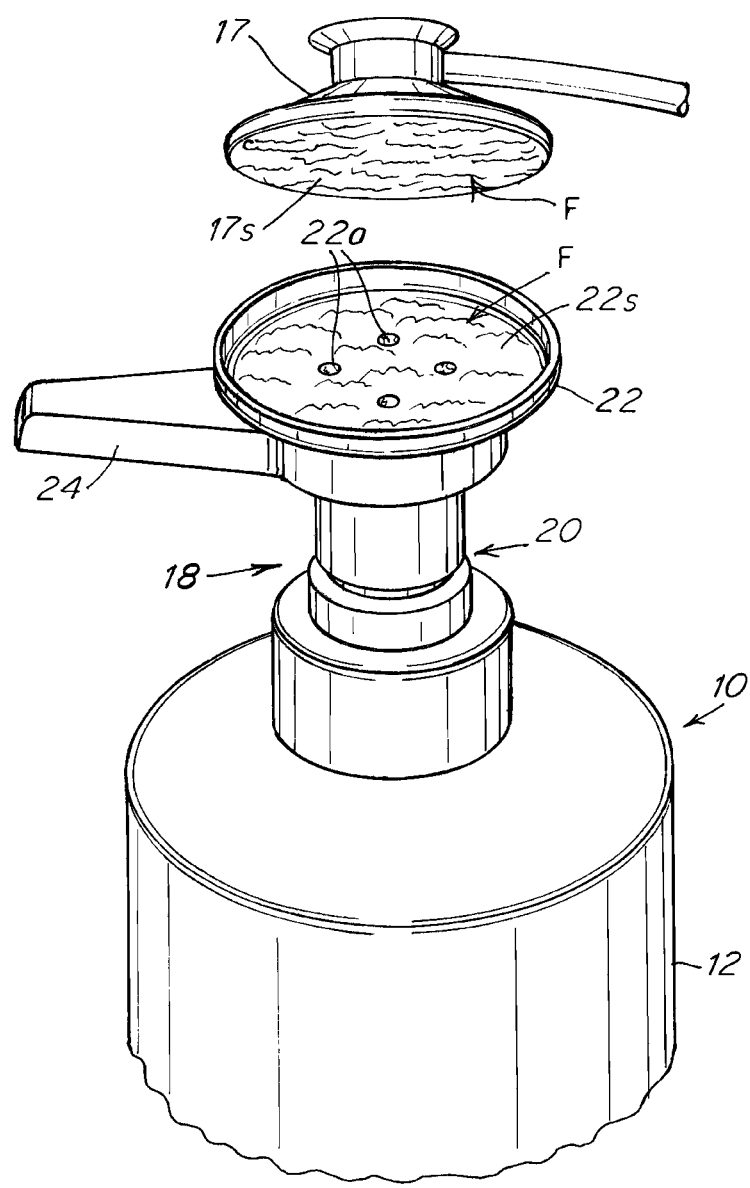
FIG. 2 is a top perspective view of the sterilization apparatus of FIG. 1 showing the configurations and relationship of the upstream facing surface of the head of the fluid delivery tube and the exterior surface of a stethoscope that is complementary in contour to the contour of the upstream facing surface of the head such that the exterior examining surface of the stethoscope can be readily manually engaged against and disengaged from contact with the upstream facing surface of the head of the tube.

FIGS. 1, 2 show a sterilization apparatus 10 comprised of fluid container 12 and a pump assembly 18 that itself is comprised of an enlarged upstream head 22 that has an upstream facing surface 22s for receiving and matably engaging a surface 17s of a selected medical or other instrument or tool 15 such as the examining surface 17s of a stethoscope that is comprised of a signal transmission cable 16 connected to an examining head 17. As shown in FIG. 1, to operate the apparatus 10 a user exerts a downstream directed force F via one of the user's hands 5 to cause the fluid delivery tube component 20 of the pump assembly 18 to be driven downstream as described below. In the embodiments described herein, when the fluid delivery tube 20 is driven in the downstream direction D, sterilization fluid F is pumped simultaneously through channels 20c leading to exit apertures 22a in head 22 as well as through a spout channel 24c that leads to an exit delivery aperture 24a such that the user can simultaneously deliver fluid F to the surface 17s of the device as well as to the other of the user's hands 6 thus enabling the user to simultaneously sterilize the device surface 17s as well as the user's hands 5, 6.

As shown in FIGS. 3-6 the pump assembly 18 is comprised of a fluid delivery tube 20 that has a central fluid delivery channel 20FC that branches at an upstream position 24b into channels 24c and 20c. The tube 20 is slidably mounted within a mount 18m and a cylinder 18c that are in turn mounted to a base 18b that is screwably engaged by threads 50t to complementary threads 12t provided on the exterior circumference of the walls of a cylindrical tubular extension 12e of the container, the tubular extension forming an aperture entrance 12ae to the interior chamber 13 of the container 12. The tube 20 is slidably mounted within the mount 18m and cylinder 18c such that the tube 20 is slidably movable in a reciprocal upstream U and downstream D direction along axis A of the tube 20.

Figure 3:
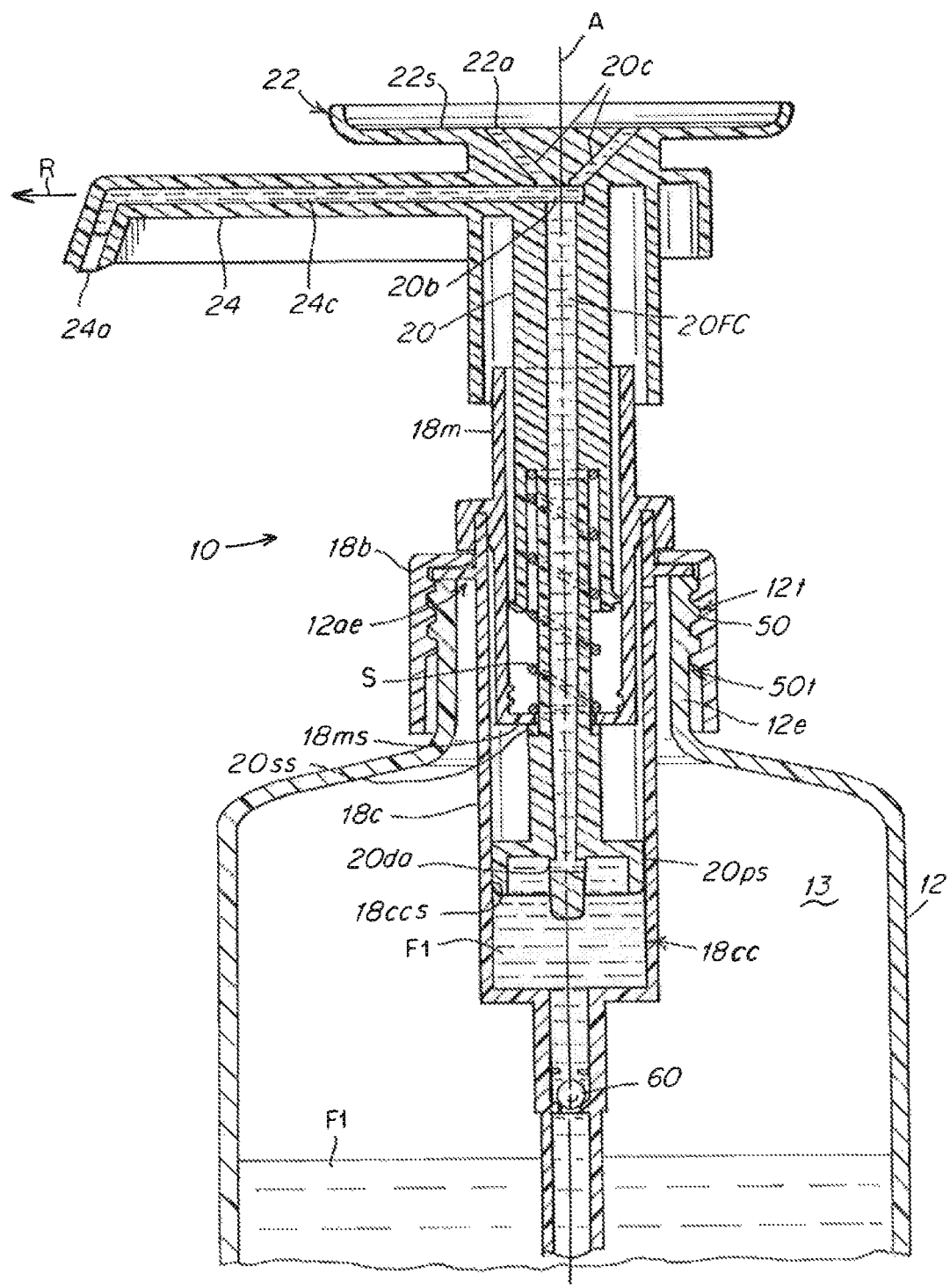
FIG. 3 is a side section view of the apparatus of FIG. 1 showing the details of the arrangement and mounting of the components of the pump assembly of the apparatus and showing the upstream downstream drivable fluid delivery tube disposed in its fully upstream start position held in such position by a spring load that biases the tube upstream and by an upstream stop that holds the tube stationary in the fully upstream position shown.

The tube 20 is constantly urged in the upstream direction U by spring S. As shown in FIG. 3, the tube 20 is disposed in its furthest upstream start position. The tube 20 is stopped from travelling any further upstream than as shown in FIG. 3 because a shoulder 20ss of the tube 20 engages a stop surface 18ms of the mount 18m that prevents the tube 20 from travelling upstream beyond the start position shown in FIG. 3.

Figure 4:
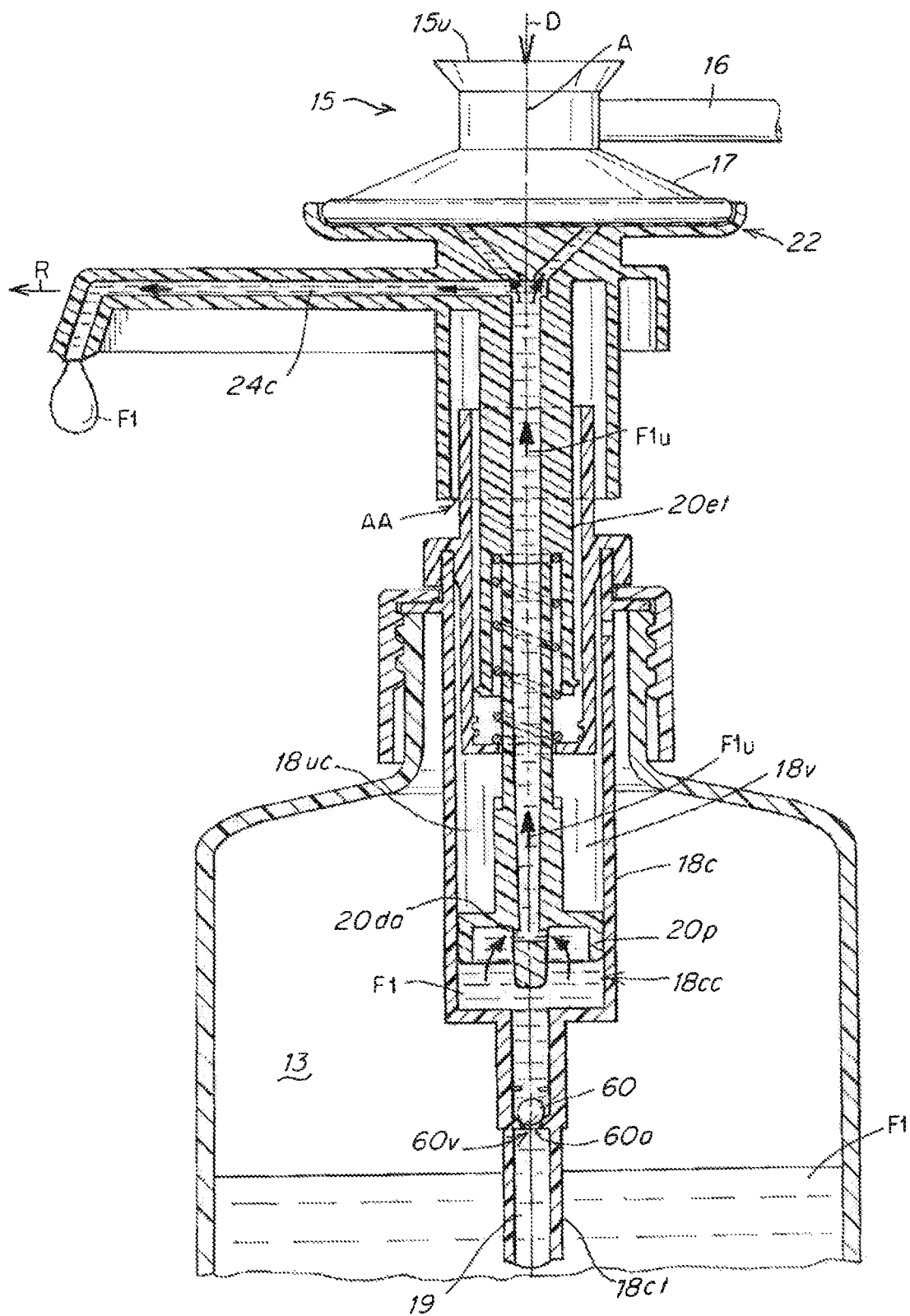
FIG. 4 is a side sectional view similar to FIG. 3 showing the complementary surface of the head of a stethoscope that it is to be sterilized manually engaged against the upstream facing surface of the head of the fluid delivery tube of the apparatus with a user applying a downstream directed force on the head of the stethoscope that translates to the slidable fluid delivery tube of the pump assembly.

As shown in FIG. 4 when a downstream directed force D is applied to the upstream end 15u of the device 15 to be sterilized, the force D is translated to the head 22 which in turn translates the force D to the elongated tube portion 20et of the tube 20 thus driving the tube 20 in a downstream direction D along axis A against the upstream directed force U of the spring S. As the tube is driven downstream D, the ball 60 component of a check valve 60v disposed at the downstream end of the cylinder 18c is forced by the downstream fluid pressure within chamber 18cc to close off the valve aperture 60a that communicates with the flow channel 19 of a downstream tube extension 18ct of the cylinder 18c in which the tube 20 is slidably mounted. With the valve 60v closed, the piston head 20p pressurizes any fluid F1 that is contained in the cylinder chamber 18cc which causes the fluid F1u to travel upstream through distal tube apertures 20da and further upstream through channel 20FC and continuously upstream F1u through channels 20c and 24c. As shown, the downstream tube extension 18ct extends downstream into the container enclosure 13 as far as possible in order to communicate with the downstream-most volume of fluid F that may be resident within the interior chamber 13.

As the tube 20 is driven downstream D as shown in FIG. 3 a vacuum 18v is created in the upstream enclosed chamber 18uc of the cylinder which in turn causes ambient air AA to be sucked into the air gaps between the sliding tube 20 and the mount 18m.

Figure 5:
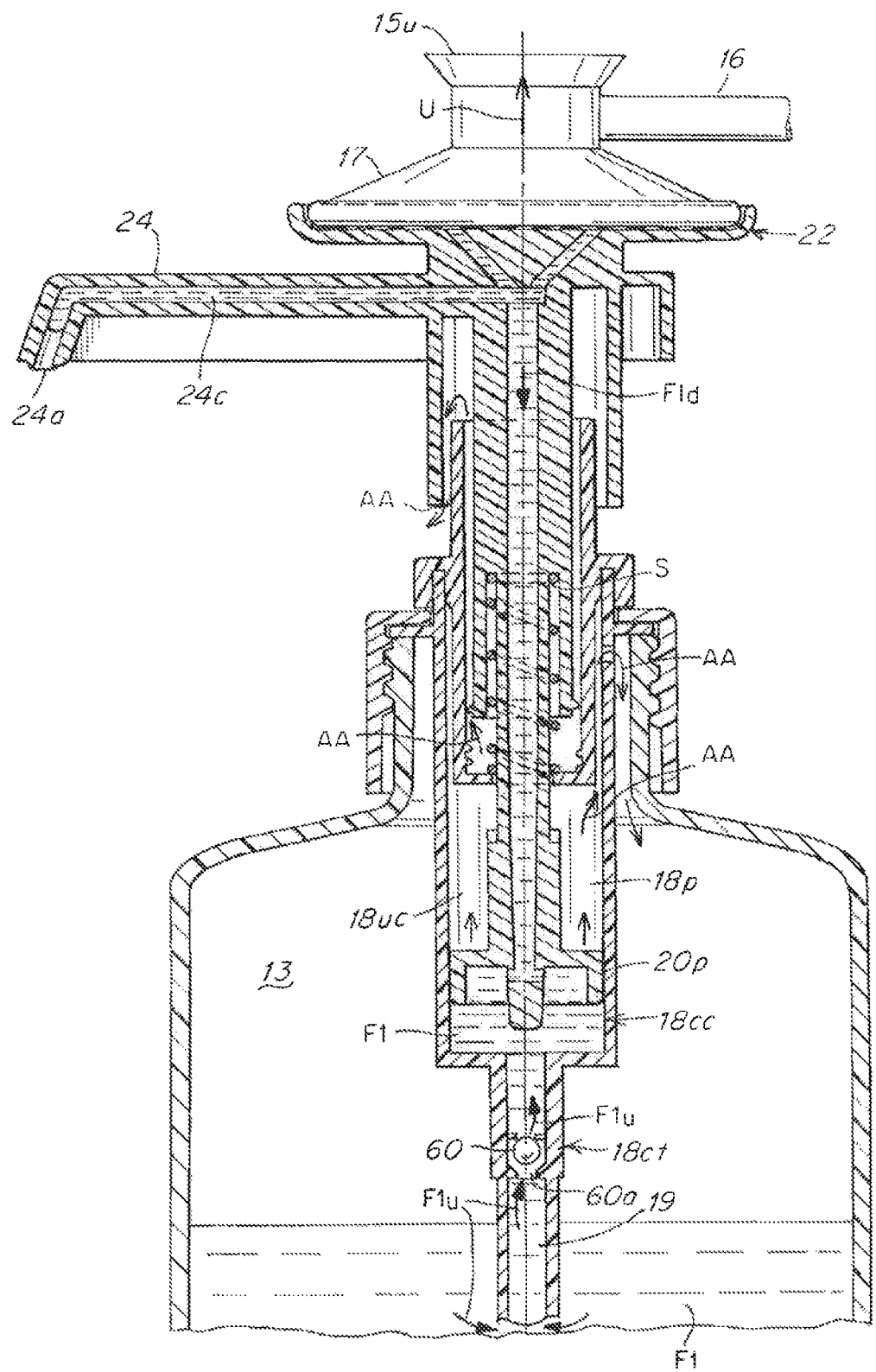
FIG. 5 is a side sectional view similar to FIG. 4 where the user has manually disengaged from exerting downstream force on the head of the stethoscope and the fluid delivery tube being driven upstream by the spring load or spring such that a vacuum is created within the downstream cylinder chamber to cause sterilization fluid to be drawn into the cylinder chamber for eventual pumping upstream on downstream driven movement of the fluid delivery tube.

As shown in FIG. 5 when the user manually disengages the upstream end 15u of the device 15 after having already driven the tube 20 downstream to the position of FIG. 4, the spring load shown as a spring S, drives or urges U the tube 20 in an upstream direction U along axis A. The upstream movement U of the tube 20 causes the fluid to create a vacuum in chamber 18cc thus causing the ball 60 to travel upwardly out of blockage engagement with valve aperture 60 thus causing fluid F contained within enclosure 13 to travel upstream F1u through channel 19 of tube extension 18ct and further upstream through now opened valve aperture 60a into chamber 18cc to replenish the fluid F that is resident in chamber 18cc for the next subsequent downstream driven D movement of the tube 20. If the top end of the tube 22 is manually disengaged as shown in FIG. 4 for a short period of time such as between about 0.5 and 6 seconds, the tube 20 is driven all the way upstream U by the spring load bias S until the tube reaches the stationary upstream-most start position shown in FIG. 3.

As the tube 20 travels upwardly U, air pressure builds 18p in chamber 18uc and thus air AA flows between the surfaces of tube 20 and mount 18m and eventually out into the ambient air as well as flows into the interior chamber 13 causing the fluid F to travel upstream through channel 19 and aperture 60a into chamber 18cc.

Figure 6:
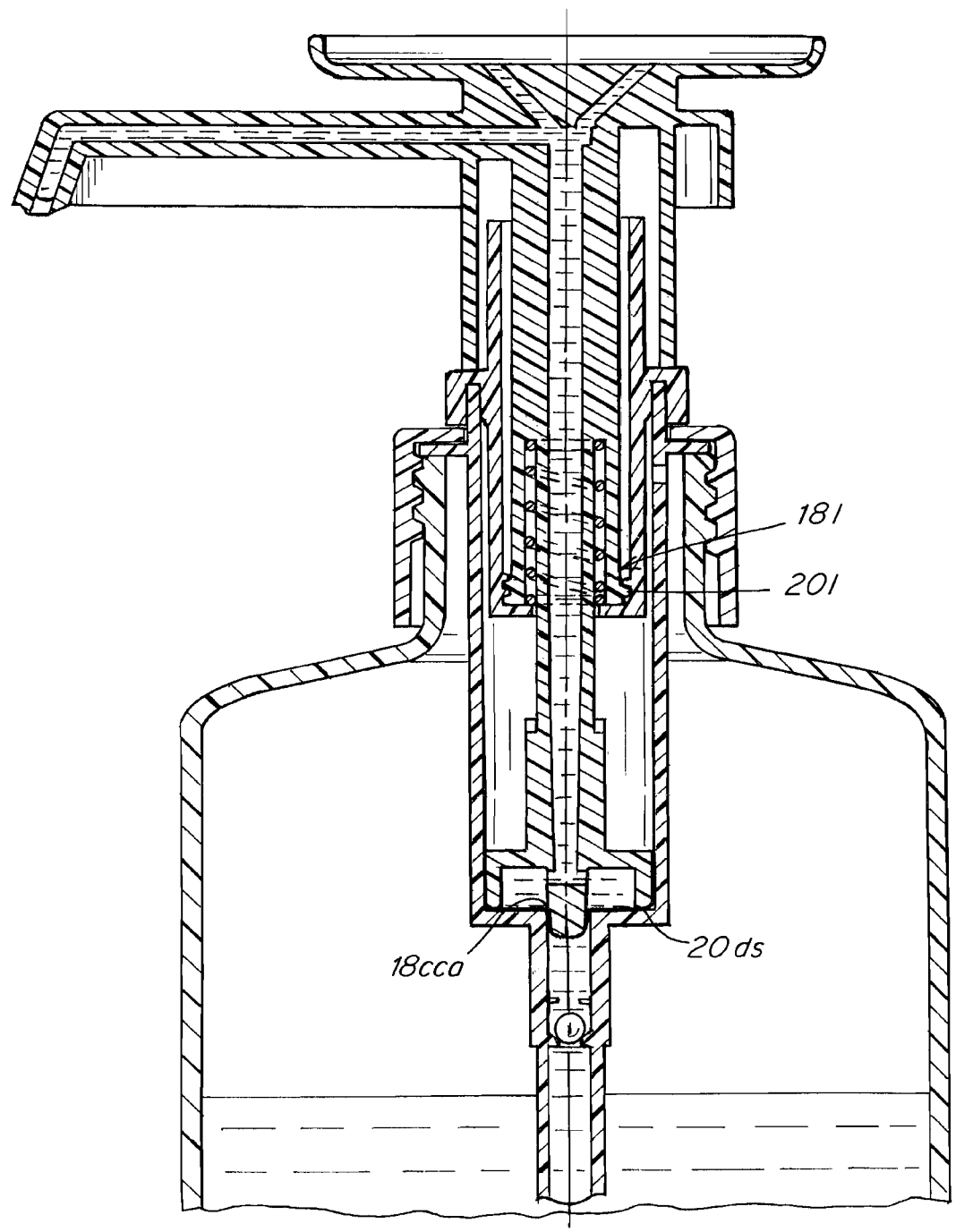
FIG. 6 is a view similar to FIGS. 4 and 5 showing the fluid delivery tube in a fully downstream locked position.

As shown in FIG. 6 if the tube 20 is manually driven even further and continuously downstream D from the position in FIG. 5 rather than being manually released as in FIG. 5 for an extended period of time in excess of from 0.5 to about 6 seconds, the tube 20 will eventually reach a maximum downstream position as shown in FIG. 6 where a lock detent 20*l* on the exterior circumference of the tube 20 engages with a complementary receiving aperture or detent 18*l* on the interior of the mount 18*m* to cause the tube to become locked in the furthest downstream position as shown in FIG. 6. When the tube 20 is so driven to the downward-most locked position of FIG. 5, a seal member 20*ds* that is mounted on the downstream tip end of the tube 20 closes off a complementary aperture 18*cca* that is disposed in the downstream end of the cylinder 18.

Figure 7:
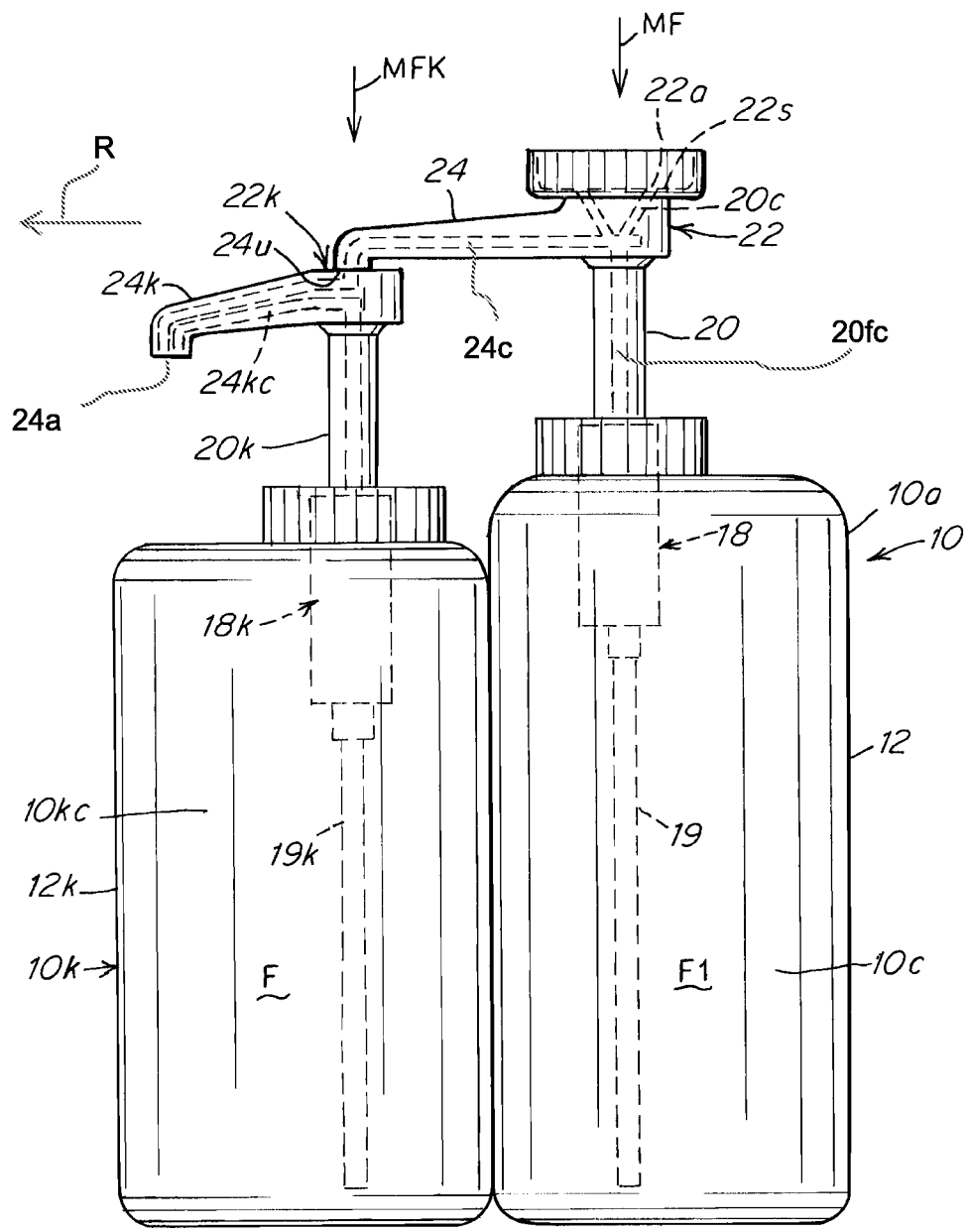
FIG. 7 is a side view of another embodiment of the invention comprised of a pair of separate fluid delivery devices each having its own separate fluid container 10, 10k and separate pump assembly, the two devices being configured and arranged side by side and attached to each other in an arrangement such that a laterally extending spout 24 of one of the two devices engages the top end surface of the spout 22k of the other device enabling the spout 22 of the first device to cause the spring loaded spout 22k of the other device to be pushed downwardly when the spout 22 of the first device is pushed downwardly and thus enabling two separate fluids contained in the fluid containers 10, 10k of each device to be delivered simultaneously through the fluid delivery tube components 20c, 24kc of each of the two separate pump assemblies of both devices.

FIG. 7 shows an alternative embodiment of the invention comprised of a pair of separate fluid delivery devices 10, 10*k* each having its own separate fluid container 12, 12*k* and separate pump assembly, the two devices being configured and arranged side by side and attached to each other in an arrangement such that a laterally extending spout 24 of one of the two devices engages the top end surface of the spout 22*k* of the other device enabling the spout 22 of the first device to cause the spring loaded spout 22*k* of the other device to be pushed downwardly when the spout 22 of the first device is pushed downwardly and thus enabling two separate fluids contained in the fluid containers 10, 10*k* of each device to be delivered simultaneously through the fluid delivery tube components 20*c*, 24*kc* of each of the two separate pump assemblies of both devices.

Figure 8:
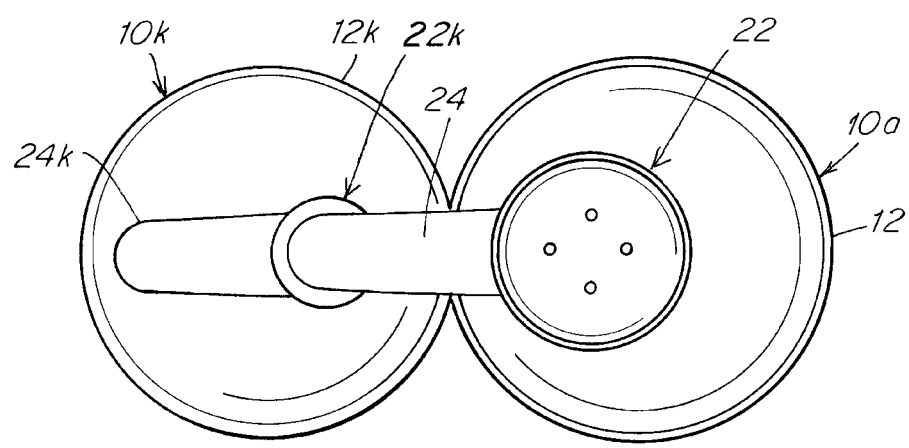
FIG. 8 is a top view of the embodiment of FIG. 7.

The two devices 10, 10*k* both separately typically include a fluid delivery pump assembly comprised of all of the same components as described above for the apparatus of FIGS. 1-6. As shown in FIG. 7 the size, height, width and length of the containers 12, 12*k*, the two spouts 24, 24*k*, the two fluid deliver tubes or channels 19, 19*k* and all other components are adapted and selected such that the containers 12, 12*k* can be attached to each other in an arrangement as shown in FIGS. 7, 8 where an undersurface 24*u* of the spout 24 one 10 of two devices 10, 10*k* can engage a top surface 22*k* of the spout 24*k* of the other device 10*k* such that when a downward force MF is exerted on the top end 22*a* of the first device 10, a downward force MFK is simultaneously exerted on the top end 22*k* of the other spout 24*k* thus simultaneously activating the pump apparatuses associated with the fluid delivery tubes 20, 20*k* and simultaneously causing each separate fluid contained in each container 12, 12*k* to be simultaneously pumped out of the separate apertures 22*a* and 24*a*.

Figure 9:
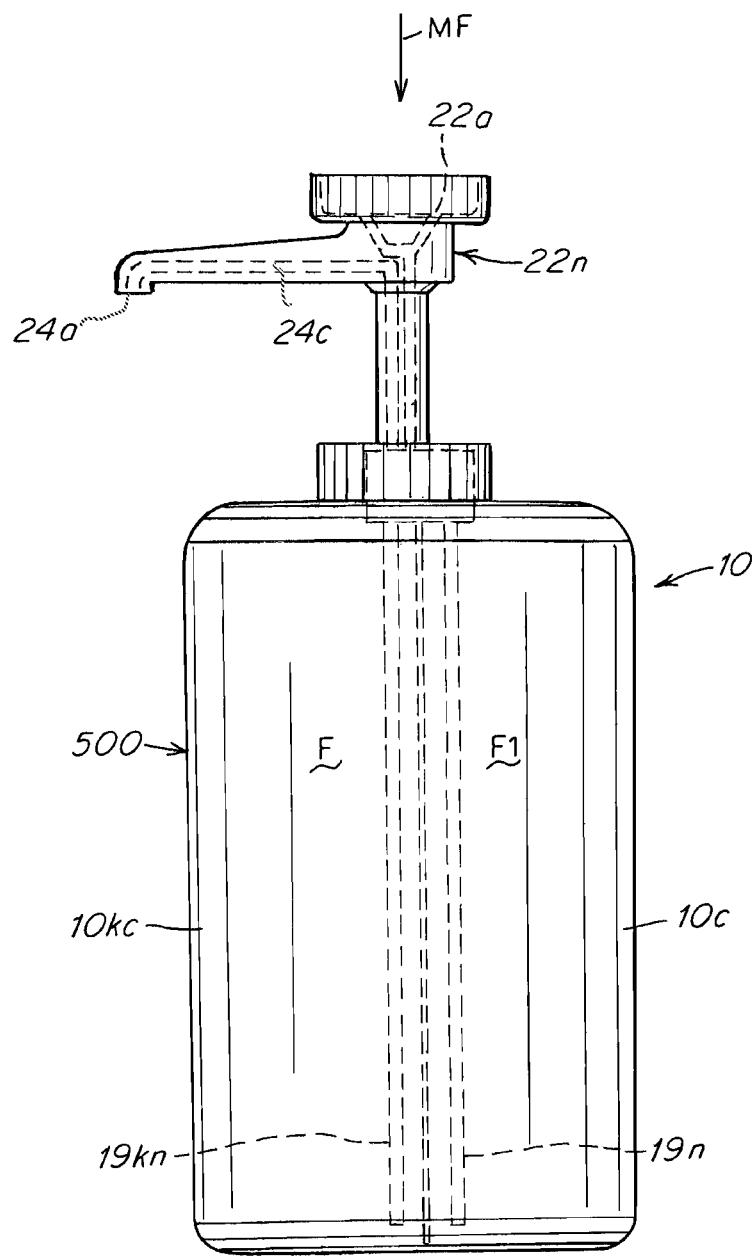
FIG. 9 is a side view of another embodiment of the invention comprised of a single fluid container 500 having two internally separated fluid chambers 10c, 10kc each containing two separate cleaning or sterilizing fluids and each pumped simultaneously through fluid delivery channels 19n 19kn respectively when a single spout 24n is pushed downwardly such that the two separate fluids are simultaneously delivered out of two separate exit apertures or orifices 22a and 24a when the spout 24n is pushed downwardly.

FIG. 9 is a side view of another embodiment of the invention comprised of a single fluid container 500 having two internally separated fluid chambers 10*c*, 10*kc* each containing two separate cleaning or sterilizing fluids and each separate fluid being pumped simultaneously through fluid delivery channels 19*n* 19*kn* respectively when a single spout 24*n* is pushed downwardly MF such that the two separate fluids are simultaneously delivered out of two separate exit apertures or orifices 22*a* and 24*a* when the spout 24*n* is pushed downwardly MF. Each fluid delivery channel 19*n*, 19*kn* is interconnected to a fluid delivery pump assembly similar to the fluid delivery pump apparatus as described with reference to FIGS. 1-6. One of the two fluids contained in one of the two chambers 10*c*, 10*kc* is selected to be suitable for cleaning or sterilizing the surface of a medical instrument (such as an alcohol containing fluid) such as a stethoscope. The other of the two fluids contained in the other of the two chambers 10*c*, 10*kc* is selected to be suitable for cleaning or sterilizing a human user's hands such as a fluid containing a selected antimicrobial agent. The fluid delivery channel that is associated with the chamber that contains the medical instrument containing fluid is delivered to and through apertures 22*a* disposed at the top end 22*n* of the spout 24*n* as described above with reference to FIGS. 1-6. The fluid delivery channel that is associated with the chamber that contains the user's hand cleaner containing fluid is delivered to and through aperture 24*a* disposed at the lateral distal end 24*n* as described above with reference to FIGS. 1-6. Thus both cleaning or sterilizing fluids are simultaneously delivered from a single container 500 as opposed to being delivered from two separate containers 10, 10*k* in the embodiment of FIGS. 7, 8.

What is claimed is:

1. An apparatus (10) for pumping first and second selected sterilizing or cleaning fluids (F1, F) by a user comprising:
   a first fluid container (12) having an enclosed interior chamber (10*c*) that receives and contains the first selected sterilizer fluid (F1),
   a second fluid container (12*k*) having an enclosed interior chamber (10*kc*) that receives and contains the second selected sterilizer fluid (F),
   a first pump assembly (18) comprising a base (18*b*) mounted to the first fluid container (12), an upstream end (22) of the first pump assembly (18) having an upstream facing surface (22*s*) having one or more apertures (22*a*) disposed in and through the upstream facing surface (22*s*), the one or more apertures (22*a*) communicating (20*c*) with the first selected sterilizer fluid (F) via a fluid flow channel (20FC) such that the first selected sterilizer fluid (F) is pumped through the one or more apertures (22*a*) on driven movement of the upstream end (22) in a downstream direction (D),
   the upstream facing surface (22*s*) of the upstream end (22) being configured to receive and engage a complementary surface (17*s*) of an external device (15) having a predetermined surface contour,
   the first pump assembly (18) being drivable downstream from a start position by manually engaging the complementary surface (17*s*) of the external device (15) against the upstream facing surface (22*s*) of the upstream end (22) and manually driving the external device (15) in the downstream direction (D) against the upstream facing surface (22*s*) of the upstream end (22),
   a second pump assembly (18*k*) mounted to the second fluid container (12*k*) including a laterally extending spout (24*k*) communicating with the second sterilizer fluid (F), the second pump assembly being manually drivable in a downstream direction (D) to pump the second selected sterilizer fluid (F) through the laterally extending spout (24*k*),
   the first and second pump assemblies (18, 18*k*) being interconnected in an arrangement adapted to simultaneously pump the first fluid (F1) through the fluid delivery apertures (22*a*) and the second fluid (F) through the laterally extending spout (24*k*) on the manual driving of the external device in the downstream direction (D), the first fluid (F1) being delivered to the complementary surface (17*s*) of the external device (15) separately from the second fluid (F).

2. The apparatus of claim 1 wherein the laterally extending spout (24*k*) terminates in a fluid delivery aperture (24*a*), the second pump assembly being adapted to deliver the second fluid (F) through the fluid delivery aperture (24*a*) of the spout (24*k*) separately from delivery of the first fluid (F1) through the fluid delivery apertures (22*a*) of the upstream end (22).

3. The apparatus of claim 1 wherein the first pump assembly (18) includes a lateral extension (24) having an undersurface (24*s*) adapted to engage a top surface (22*k*) of the laterally extending spout (24*k*), the laterally extending spout (24*k*) being driven in a downstream direction (D) together with the upstream end (22) on the manual driving of the external device against the upstream end (22) in the downstream direction (D).

4. A method of performing a sterilization process comprising a user manually driving the external device (15) in the downstream direction (D) against the upstream facing surface (22*s*) of an apparatus according to claim 1.

5. An apparatus (10) for pumping first and second selected sterilizing or cleaning fluids (F1, F) by a user comprising:
- a first fluid container (12) having an enclosed interior chamber (10*c*) that receives and contains the first selected sterilizer fluid (F1),
- a second fluid container (12*k*) having an enclosed interior chamber (10*kc*) that receives and contains the second selected sterilizer fluid (F),
- a first pump assembly (18) comprising a base (18*b*) mounted to the first fluid container (12), an upstream end (22) of the first pump assembly (18) having an upstream facing surface (22*s*) communicating (20*c*) with the first selected sterilizer fluid (F) via a fluid flow channel (20FC) such that the first selected sterilizer fluid (F) is pumped to the upstream facing surface (22*s*) on driven movement of the upstream end (22) in a downstream direction (D),
- the upstream facing surface (22*s*) of the upstream end (22) being configured to receive and engage a complementary surface (17*s*) of an external device (15) having a predetermined surface contour,
- the first pump assembly (18) being drivable downstream from a start position by manually engaging the complementary surface (17*s*) of the external device (15) against the upstream facing surface (22*s*) of the upstream end (22) and manually driving the external device (15) in the downstream direction (D) against the upstream facing surface (22*s*) of the upstream end (22),
- a second pump assembly (18*k*) mounted to the second fluid container (12*k*) including a laterally extending spout (24*k*) communicating with the second sterilizer fluid (F), the second pump assembly being manually drivable in a downstream direction (D) to pump the second selected sterilizer fluid (F) through the laterally extending spout (24*k*), the laterally extending spout (24*k*) terminating in a fluid delivery aperture (24*a*), the second pump assembly being adapted to deliver the second fluid (F) through the fluid delivery aperture (24*a*) of the spout (24*k*) separately from delivery of the first fluid (F1) to the upstream facing surface (22*s*),
- the first and second pump assemblies (18, 18*k*) being interconnected in an arrangement adapted to simultaneously pump the first fluid (F1) to the upstream facing surface (22*s*) and the second fluid (F) through the laterally extending spout (24*k*) on the manual driving of the external device in the downstream direction (D).

6. The apparatus of claim 5 wherein the upstream facing surface (22*s*) includes one or more apertures (22*a*) disposed in and through the upstream facing surface (22*s*), the first fluid (F1) being delivered through the one or more apertures (22*a*) separately from delivery of the second fluid (F) through the fluid delivery aperture (24*a*) of the laterally extending spout (24*k*),
the laterally extending spout (24*k*) terminates in a fluid delivery aperture (24*a*), the second pump assembly being adapted to deliver the second fluid (F) through the fluid delivery aperture (24*a*) of the spout (24*k*) separately from delivery of the first fluid (F1) through the fluid delivery apertures (22*a*) of the upstream end (22).

7. The apparatus of claim 5 wherein the first pump assembly (18) includes a lateral extension (24) having an undersurface (24*s*) adapted to engage a top surface (22*k*) of the laterally extending spout (24*k*), the laterally extending spout (24*k*) being driven in a downstream direction (D) together with the upstream end (22) on the manual driving of the external device against the upstream end (22) in the downstream direction (D).

8. A method of performing a sterilization process comprising a user manually driving the external device (15) in the downstream direction (D) against the upstream facing surface (22*s*) of an apparatus according to claim 5.

* * * * *